United States Patent [19]

Rosenblatt et al.

[11] 3,949,008

[45] Apr. 6, 1976

[54] PURIFICATION OF CRUDE DINITROTOLUENE BY EXTRACTION WITH $C_5$-$C_8$ ALKANES

[75] Inventors: David H. Rosenblatt, Baltimore; William H. Dennis, Jr., Braddock Heights, both of Md.

[73] Assignee: The United States of America as represented by the Secretary of the Army, Washington, D.C.

[22] Filed: Dec. 5, 1974

[21] Appl. No.: 529,972

[52] U.S. Cl. .............................. 260/645; 260/705
[51] Int. Cl.² .................................. C07C 79/10
[58] Field of Search ............................... 260/645

[56] References Cited

FOREIGN PATENTS OR APPLICATIONS

| | | | |
|---|---|---|---|
| 752,608 | 7/1956 | United Kingdom | 260/645 |
| 1,054,571 | 1/1967 | United Kingdom | 260/645 |

*Primary Examiner*—Leland A. Sebastian
*Attorney, Agent, or Firm*—Nathan Edelberg; Robert P. Gibson; A. Victor Erkkila

[57] ABSTRACT

2,4- and 2,6-Dinitrotoluenes mixed with small amounts of isomeric dinitrotoluene impurities are extracted with an alkane of 5 to 8 carbon atoms, whereby the isomeric dinitrotoluene impurities are removed.

6 Claims, No Drawings

PURIFICATION OF CRUDE DINITROTOLUENE BY EXTRACTION WITH C₅-C₈ ALKANES

BACKGROUND OF THE INVENTION

Dinitrotoluene is conventionally manufactured by nitrating toluene with a mixture of nitric and sulfuric acids. The crude dinitrotoluene thus obtained contains the desired 2,4- and 2,6-dinitrotoluene isomers along with small amounts, usually less than 5% of isomeric dinitrotoluene impurities, notably the 2,3-, 2,5- and 3,4-dinitrotoluene isomers (so-called "meta" isomers). Dinitrotoluene is valuable as an intermediate in the manufacture of 2,4,6-trinitrotoluene (TNT) employed as an explosive for military use. The TNT obtained by nitration of crude dinitrotoluene contains the desired 2,4,6-isomer along with a small amount, usually about 3-5% of the undesired 2,4,5-, 2,3,4, and 2,3,6-trinitrotoluene isomers, which result from the nitration of the aforesaid "meta" isomers present in crude dinitrotoluene. At present TNT is purified by treatment with a hot solution of sodium sulfite (sellite) solution, which removes the undesired TNT isomers but results in a very concentrated and intensely reddish colored solution whose diposal is costly and contributes to a serious pollution of streams into which it is discharged.

It is thus evident that the removal of the so-called meta isomers in crude dinitrotoluene is highly desirable, since it would permit the production of military grade 2,4,6-TNT directly and thus eliminate the need for sellite purification and attendant purification problems.

SUMMARY OF THE INVENTION

Accordingly, it is an object of the present invention to provide a process for purifying crude dinitrotoluene whereby a purified product can be obtained, which meets the military specification for propellant grade dinitrotoluene. It is a further object of the invention to provide a process for purifying crude dinitrotoluene to produce a purified product, which on nitration yields acceptable military grade 2,4,6-TNT directly and thus does not require purification by means of hot sodium sulfite solution (sellite process). Other objects will become apparent from the following description of the invention.

In accordance with the process of the present invention, crude dinitrotoluene, consisting of 2,4- and 2,6-dinitrotoluenes mixed with small amounts of isomeric dinitrotoluene impurities, is extracted with an alkane of 5 to 8 carbon atoms or a mixture of such alkanes, whereby the isomeric dinitrotoluenes are removed and a purified product containing an increased ratio of 2,4-dinitrotoluene to 2,6-dinitrotoluene is obtained.

DETAILED DESCRIPTION OF THE INVENTION

The following examples illustrate specific embodiments of the method of carrying out the process of the present invention.

The procedure employed in the examples was as follows. Crude dinitrotoluene was vigorously agitated with an amount ranging from about 5 to about 25 times its weight of n-hexane at room temperature for about 3 minutes. The undissolved, purified dinitrotoluene was then separated by filtration from the liquid hexane solution of extracted impurities.

The following table sets forth the compositions of the crude dinitrotoluene (DNT) starting material and the purified products obtained by use of the various proportions of n-hexane extractant. As shown in the table, the purified DNT products contained 50-85% less of the undesired meta DNT isomers and a higher ratio of 2,4- to 2,6-DNT isomers as well as a higher and narrower melting point range than the crude DNT staring material. The purified DNT obtained in example 3 meets the U.S. Army military specifications for propellant grade DNT; and it can be nitrated to yield military grade 2,4,6-TNT directly without the need for purification by the sellite process.

|  | Crude DNT | Example 1 | Example 2 | Example 3 |
|---|---|---|---|---|
| Wt. Ratio DNT/n-Hexane | — | 1/6.6 | 1/13.2 | 1/26 |
| Analyses* 2,4-DNT | 85.96% | 94.22% | 96.76% | 98.47% |
| 2,6-DNT | 12.55 | 5.04 | 2.81 | 1.30 |
| 3,4-DNT | 1.07 | 0.55 | 0.34 | 0.19 |
| 2,3-DNT | 0.35 | 0.18 | 0.06 | 0.03 |
| 2,5-DNT | 0.06 | 0.01 | 0.02 | 0.01 |
| Melting Point | 55–65°C. | 65–69°C. | 66–70°C. | 63–70°C. |
| Yield of Purified DNT | — | 70% | 71% | 58% |

*The analyses were performed as follows:

An aliquot of the purified DNT (50 mg) was dissolved in 0.5 ml of benzene and analyzed by gas chromatography, wherein the isomers were separated isothermally using a 5 foot column glass U tube of ¼ inch I.D. containing 5% Carbowax 20M on 60/80 mesh Chromasorb W (AW) at 150°C. under atmospheric pressure. The order of elution was (from first to last) 2,6-DNT; 2,5-DNT; 2,4-DNT; 2,3-DNT; and 3,4-DNT. (Carbowax 20M is a polyethyleneglycol of molecular weight 20,000, manufactured by the Union Carbide Corporation. Chromasorb W (AW) is an acid washed diatomaceous earth manufactured by the Johns-Manville Corp.)

Similar results are obtained by employing other alkanes of 5 to 8 carbon atoms, including mixtures of such alkanes, in place of n-hexane, as illustrated in the foregoing examples, such as for example, n-pentane, n-heptane, n-octane, 2-methylpentane, 2-ethylhexane, petroleum either (b.p. 40°–60°C., a petroleum fraction consisting essentially of C₅ to C₆ alkanes) and naphtha (b.p. 70°–90°C., a petroleum fraction of C₆ to C₇ alkanes).

In carrying out the process of the present invention the impure dinitrotoluene is suspended generally in about from 5 to 30 times its weight of the liquid alkane. The suspension is preferably vigorously agitated to provide intimate contact between the dinitrotoluene and the liquid alkane extractant and thus promote rapid removal of the aforesaid isomeric impurities. The process is efficiently and economically carried out as substantially atmospheric temperature and pressure, although moderately elevated temperatures and pressures can be employed, if desired. The amount of the isomeric impurities removed is increased as the ratio of alkane to dinitrotoluene is increased. However, the use of substantially more than 30 parts of alkane extractant per part by weight of the impure dinitrotoluene results in excessive dissolution and loss of the desired 2,4-dinitrotoluene isomer in the alkane extractant and hence is undesired. Likewise, the use of substantially less than 5 parts of alkane per part of the impure dinitrotoluene is undesired, since it provides insufficient removal of said isomeric impurities. Accordingly, in the process of the present invention it is generally preferred to suspend the impure dinitrotoluene in about from 15 to 30 times its weight of the liquid alkane extractant.

The foregoing disclosure is merely illustrative of the principles of this invention and are not to be interpreted in a limiting sense. We wish it to be understood that we do not desire to be limited to exact details of construction shown and described, because obvious modification will occur to a person skilled in the art.

What is claimed is:

1. A process for purifying an impure dinitrotoluene, consisting of 2,4- and 2,6-dinitrotoluene isomers mixed with a small amount of isomeric dinitrotoluene impurities, which comprises suspending the impure dinitrotoluene in a liquid consisting essentially of an alkane containing between 5 and 8 carbon atoms and separating the undissolved purified dinitrotoluene from the liquid alkane, whereby the isomeric dinitrotoluene impurities are removed in the alkane extract and a purified dinitrotoluene product containing a reduced amount of isomeric dinitrotoluene impurities and an increased ratio of 2,4- to 2,6-dinitrotoluenes is obtained.

2. The process of claim 1, wherein the impure dinitrotoluene contains not more than about 2% of said isomeric dinitrotoluene impurities and more than about 80% of 2,4-dinitrotoluene.

3. The process of claim 2, wherein the impure dinitrotoluene is suspended in about from 5 to 30 times its weight of said liquid alkane.

4. The process of claim 3, wherein the alkane is n-hexane.

5. The process of claim 3, wherein the alkane is a petroleum ether consisting essentially of a mixture of pentanes and hexanes.

6. The process of claim 3, wherein the impure dinitrotoluene is contacted with the liquid alkane at ambient temperature.

* * * * *